US009347921B2

United States Patent
Probst

(10) Patent No.: US 9,347,921 B2
(45) Date of Patent: May 24, 2016

(54) METHOD FOR FILTERING A CHROMATOGRAM

(75) Inventor: Frank Probst, Herxheim bei Landau/Pfalz (DE)

(73) Assignee: Siemens Aktiengesellschaft, Munich (DE)

( * ) Notice: Subject to any disclaimer, the term of this patent is extended or adjusted under 35 U.S.C. 154(b) by 973 days.

(21) Appl. No.: 13/388,119

(22) PCT Filed: Jul. 29, 2010

(86) PCT No.: PCT/EP2010/061005
§ 371 (c)(1),
(2), (4) Date: Apr. 11, 2012

(87) PCT Pub. No.: WO2011/012668
PCT Pub. Date: Feb. 3, 2011

(65) Prior Publication Data
US 2012/0191372 A1 Jul. 26, 2012

(30) Foreign Application Priority Data

Jul. 31, 2009 (DE) .......................... 10 2009 035 587

(51) Int. Cl.
*G01N 30/86* (2006.01)
(52) U.S. Cl.
CPC ........ *G01N 30/8617* (2013.01); *G01N 30/8693* (2013.01)
(58) Field of Classification Search
CPC ..................................................... G01N 30/86
USPC ............................................................ 702/32
See application file for complete search history.

(56) References Cited

U.S. PATENT DOCUMENTS

| | | | | |
|---|---|---|---|---|
| 4,837,726 A * | 6/1989 | Hunkapiller | ..................... | 702/32 |
| 4,852,017 A * | 7/1989 | Hunkapiller | ..................... | 702/20 |
| 5,885,841 A * | 3/1999 | Higgs et al. | ..................... | 436/89 |
| 6,151,415 A * | 11/2000 | Acharya et al. | ............... | 382/255 |
| 6,379,970 B1 * | 4/2002 | Liebler et al. | ................... | 436/86 |
| 6,393,368 B1 * | 5/2002 | Ito et al. | .......................... | 702/22 |
| 6,873,915 B2 * | 3/2005 | Hastings | .......................... | 702/22 |

(Continued)

FOREIGN PATENT DOCUMENTS

| | | |
|---|---|---|
| EP | 0222612 | 5/1987 |
| EP | 0295966 | 12/1988 |

(Continued)

*Primary Examiner* — Sujoy Kundu
*Assistant Examiner* — Catherine Rastovski
(74) *Attorney, Agent, or Firm* — Cozen O'Connor

(57) ABSTRACT

Low-complexity, application-independent fixation of a chromatogram is achieved by a) determining a limit frequency under the assumption that the shape of the peaks in the chromatogram corresponds approximately to a Gaussian function having a standard deviation and the Fourier transform of the Gaussian function describes the frequency spectrum of a peak, at which limit frequency the Fourier transform has decreased to a predetermined limit value, b) determining the height, width, and retention time of each individual peak from the chromatogram, or a chromatogram taken previously under the same conditions, c) determining a constant factor based on a first predetermined relationship, d) determining the functional dependency of the limit frequency on the retention time as a variable quantity based on a second predetermined relationship, and e) filtering the chromatogram with the limit frequency depending on the retention time as the variable quantity using a low-pass filter.

2 Claims, 3 Drawing Sheets

(56) References Cited

U.S. PATENT DOCUMENTS

| | | | |
|---|---|---|---|
| 6,936,814 B2* | 8/2005 | Hastings | 250/282 |
| 6,944,549 B2* | 9/2005 | McClure | 702/22 |
| 6,982,414 B2* | 1/2006 | Bateman et al. | 250/282 |
| 7,198,893 B1* | 4/2007 | Koster et al. | 435/6.16 |
| 7,628,914 B2* | 12/2009 | Norton | 210/198.2 |
| 7,759,065 B2* | 7/2010 | Koster | 435/5 |
| 7,928,363 B2* | 4/2011 | Bateman | 250/283 |
| 7,982,181 B1* | 7/2011 | Senko | 250/282 |
| 8,017,908 B2 | 9/2011 | Gorenstein et al. | |
| 8,081,792 B2* | 12/2011 | Moon et al. | 382/100 |
| 8,237,106 B2* | 8/2012 | Castro-Perez et al. | 250/281 |
| 2003/0203502 A1* | 10/2003 | Zenhausern et al. | 436/164 |
| 2004/0199336 A1* | 10/2004 | Ito et al. | 702/32 |
| 2005/0143948 A1* | 6/2005 | Ito et al. | 702/134 |
| 2005/0265629 A1* | 12/2005 | Fu et al. | 382/275 |
| 2006/0020401 A1 | 1/2006 | Davis et al. | |
| 2007/0211928 A1* | 9/2007 | Weng et al. | 382/128 |
| 2007/0278395 A1* | 12/2007 | Gorenstein et al. | 250/282 |
| 2008/0109174 A1* | 5/2008 | Chau | 702/27 |
| 2008/0270083 A1* | 10/2008 | Lange et al. | 702/193 |
| 2008/0306694 A1* | 12/2008 | Izmailov et al. | 702/19 |
| 2008/0306696 A1* | 12/2008 | Izmailov et al. | 702/32 |
| 2009/0294645 A1* | 12/2009 | Gorenstein et al. | 250/282 |
| 2010/0161238 A1* | 6/2010 | Cappadona et al. | 702/19 |
| 2010/0280811 A1* | 11/2010 | Gorenstein et al. | 703/12 |
| 2010/0283785 A1* | 11/2010 | Satulovsky | 345/440 |

FOREIGN PATENT DOCUMENTS

| | | |
|---|---|---|
| EP | 0296781 | 12/1988 |
| WO | WO 2005079263 | 9/2005 |

* cited by examiner

METHOD FOR FILTERING A CHROMATOGRAM

CROSS-REFERENCE TO RELATED APPLICATIONS

This is a U.S. national stage of application No. PCT/EP2010/061005 filed 29 Jul. 2010. Priority is claimed on German Application No. 10 2009 035 587.1 filed 31 Jul. 2009, the content of which is incorporated herein by reference in its entirety.

BACKGROUND OF THE INVENTION

1. Field of the Invention

The invention relates to digital signal processing and, more particularly, to a method for filtering a chromatogram.

2. Description of the Related Art

In chromatography, a sample of a substance mixture to be analyzed is passed through a chromatographic separating device. Because of different migration rates through the separating device, the analytes, i.e., the individual substances of the substance mixture, reach the output of the separating device at different times and are successively detected at this point by a suitable detector. The time that the analytes require to migrate through the separating device is referred to as the retention time. As its measurement signal, the detector generates a chromatogram that consists of a baseline and a number of peaks corresponding to the separated substances. In practice, the chromatogram is affected by noise, with the individual peaks standing out more or less clearly from the signal noise. The detection limit of an analyte is defined as a predetermined multiple of the noise. That is, the peak height measured from the noise-free baseline, i.e., from the average value of the noise, must be at least the predetermined multiple of the noise.

With well-resolved peaks, the peak area above the noise-free baseline is proportional to the concentration of the analyte. The peak area, in contrast to the peak height, provides accurate measurement results even for nonsymmetrical peaks.

In order to isolate the analytical information, i.e., the peaks, the chromatogram is smoothed by lowpass filtering. Smoothing algorithms suitable for this purpose are, for example, a moving average or the Savitzky-Golay filter. The lower the limit frequency of the lowpass filter or the greater the filter length of the Finite Impulse Response (FIR) filter used, the better the smoothing that can be obtained. With increasing smoothing, however, the peaks may also be deformed so that the measurement accuracy is reduced. Depending on which substance mixtures are to be analyzed, the measurement applications, for example, different separating columns with different interconnection, and measurement conditions within an application, for example, different temperature and pressure profiles in the separating device, may be very different and lead to correspondingly different chromatograms, which necessitates differently dimensioned filters for smoothing the chromatograms.

SUMMARY OF THE INVENTION

It is therefore an object of the invention to permit low-complexity, application-independent and universal filtering of chromatograms.

This and other objects and advantages are achieved in accordance with the invention by a method comprising the following steps:

a) under an assumption that the shape of the peaks (P) in a chromatogram respectively corresponds approximately to a Gaussian function $f(t, \sigma)$ with standard deviation $\sigma$ and the Fourier transform $F(f, \sigma)$ of the Gaussian function $f(t, \sigma)$ describes the frequency spectrum of a peak (P), a limit frequency $f_G(F_G, \sigma)$ at which the Fourier transform $F(f, \sigma)$ has decreased to a predetermined limit value $F_G = F(f_G, \sigma_0)$ is determined, b) the height $h_0$, width $b_0$ and retention time $t_{R0}$ of an individual peak ($P_0$) of the chromatogram, or of a chromatogram previously recorded under the same conditions, are determined, c) the constant factor K is determined with the aid of the relation $\sigma_0/h_0 = K \cdot t_{R0}$, d) the functional dependency of the limit frequency $f_G(F_G, t_R)$ on the retention time $t_R$ as a variable quantity is determined with the aid of the relation $\sigma/h = K \cdot t_R$ and e) the chromatogram is lowpass-filtered with the limit frequency $f_G(F_G, t_R)$ as a function of the retention time $t_R$.

The invention is based on the observation that the ratio of width b to height h of a peak increases linearly with the retention time $t_R$, so that $b/h = K' \cdot t_R$. Apart from a few exceptions, the shape of the peak becomes ever closer to a classical Gaussian distribution as the retention time $t_R$ increases. Consequently, a peak of width b can be described with sufficient accuracy by a Gaussian function $f(t, \sigma)$. Depending on where the peak is measured, the peak width b is a multiple of the standard deviation $\sigma$, and is, for example, at half peak height $b = 2\sigma\sqrt{2\ln 2} = 2.355\sigma$. The aforementioned ratio of width b to height h of a peak can therefore also be described by $\sigma/h = K \cdot t_R$.

The height h and the standard deviation $\sigma$ of the Gaussian function are associated with one another by the relation $h = 1/(\sigma\sqrt{2\pi})$. The factor K can therefore be determined with the aid of the measured height $h_0$, width $b_0$ and retention time $t_{R0}$ of a selected individual peak, where the standard deviation $\sigma_0$ is calculated from the peak width $b_0$.

It is now possible to express the Gaussian function $f(t, \sigma)$ in a functional dependency on the retention time $t_R$ as a variable quantity: $f(t, t_R)$. The Fourier transform $F(f, t_R)$ of the Gaussian function $f(t, t_R)$ then describes the frequency spectrum of a peak as a function of the retention time $t_R$. A limit value $F_G$ is now established for this frequency spectrum $F(f, t_R)$, with frequencies f having transforms above this limit value $F_G$ being regarded as analytical information and frequencies f having transforms below this limit value $F_G$ being regarded as noise. Both the limit value $F_G$ and the limit frequency $f_G$ associated with it are dependent on the retention time, i.e., $F_G = F_G(t_R)$ and $f_G = f_G(t_R)$. The chromatogram is now smoothed by lowpass filtering with the limit frequency $f_G(t_R)$ thus determined as a function of the retention time $t_R$.

The individual peak that is used for determining the factor K may be selected from the chromatogram currently to be evaluated or from a chromatogram recorded earlier for the same measurement applications and under the same measurement conditions. The latter includes, for example, the option of obtaining the values of the peak from any available sources in standard measurement applications.

In accordance with the above-described method step d), the functional dependency $f_G(F_G, t_R)$ of the limit frequency $f_G$ on the retention time $t_R$ as a variable quantity is determined with the aid of the relationship $\sigma/h = K \cdot t_R$. The latter includes the option of performing the conversion of the functional dependency on the peak width b (or standard deviation $\sigma$) into the functional dependency on the retention time $t_R$ even earlier, such as by using the Gaussian function $(f(t, \sigma) \rightarrow f(t, t_R))$ or its Fourier transform $(F(f, \sigma) \rightarrow F(f, t_R))$.

The lowpass filtering, for example, a moving average, is preferably performed by an FIR filter whose filter length is varied according to the limit frequency $f_G$ ($F_G$, $t_R$) as a function of the retention time $t_R$.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The further explanations of the invention will refer to the figures of the drawing; in detail.

DESCRIPTION OF THE PREFERRED EMBODIMENTS

Figure 1:
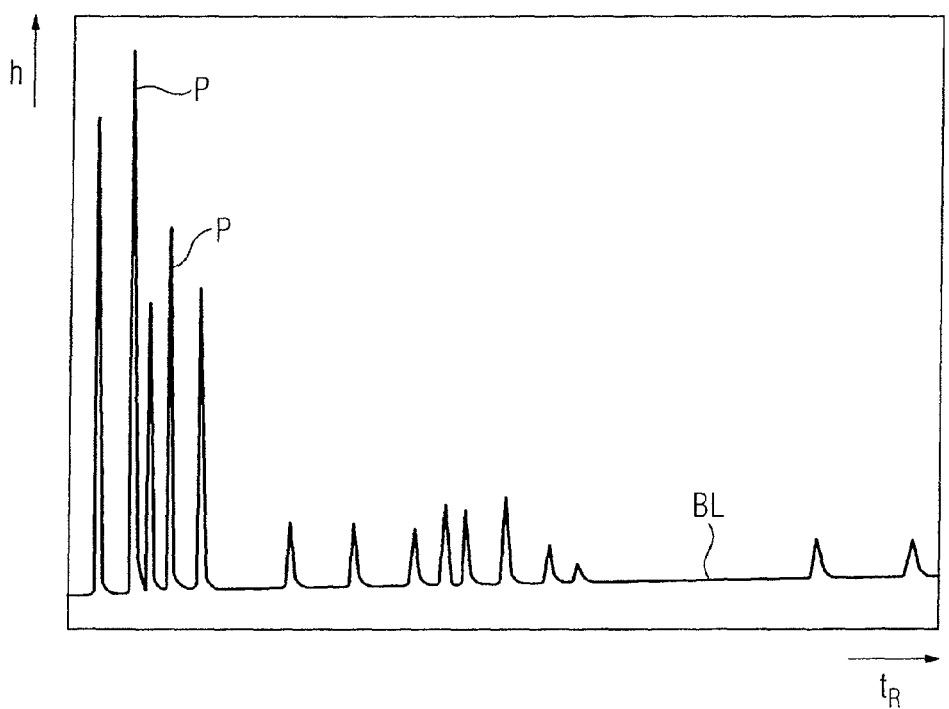
FIG. 1 is an exemplary graphical plot of a chromatogram comprising a multiplicity of peaks.

FIG. 1 is a graphical plot of a conventional chromatogram, which consists of a baseline BL and a multiplicity of peaks P with different peak heights h and retention times $t_R$. Each peak P results from the detection of a specific analyte, the area of the peak P above the baseline BL being proportional to the concentration of the analyte. With reference to FIG. 1, as can be seen, the relative width, i.e., the width of the peak P in relation to the peak height, increases with an increasing retention time $t_R$, the shape of the peak P becoming ever closer to a classical Gaussian distribution. With respect to their shape, the peaks P can therefore be described as follows by a Gaussian function:

$$f(t, \sigma) = \frac{1}{\sqrt{\sigma\sqrt{2\Pi}}} e^{-\frac{1}{2}\left(\frac{t-t_B}{\sigma}\right)^2}, \quad \text{Eq. 1}$$

where $\sigma$ denotes the standard deviation.

The frequency spectrum of an individual peak P is given by the Fourier transform F (f, $\sigma$) of the Gaussian function $f$ (t, $\sigma$) as:

$$F(f, \sigma) = \int_{-\infty}^{+\infty} f(t, \sigma) e^{-j2\pi ft} dt = e^{-\frac{1}{2}(2\pi f\sigma)^2}. \quad \text{Eq. 2}$$

The frequency spectrum simultaneously represents the amplitude characteristic, which in signal processing technology is conventionally indicated in decibels:

$$\frac{F(f, \sigma)}{dB} = 20\log_{10}(F(f, \sigma)) \quad \text{Eq. 3}$$
$$= 20\log_{10}(e^{-\frac{1}{2}(2\pi f\sigma)^2})$$
$$= 20\left(-\frac{1}{2}(2\pi f\sigma)^2\right)\log_{10}e$$
$$= -4.343 \cdot (2\pi f\sigma)^2$$

As previously explained, it has been observed that the ratio of width b to height h of a peak P increases linearly with the retention time $t_R$, so that:

$$b/h = K' \cdot t_R \text{ or } \sigma/h = K \cdot t_R. \quad \text{Eq. 4}$$

With Eq. 4, Eq. 3 can be rewritten as follows:

$$\frac{F(f, t_R)}{dB} = -4.343 \cdot (2\pi f \cdot h \cdot K \cdot t_R)^2. \quad \text{Eq. 5}$$

Figure 2:
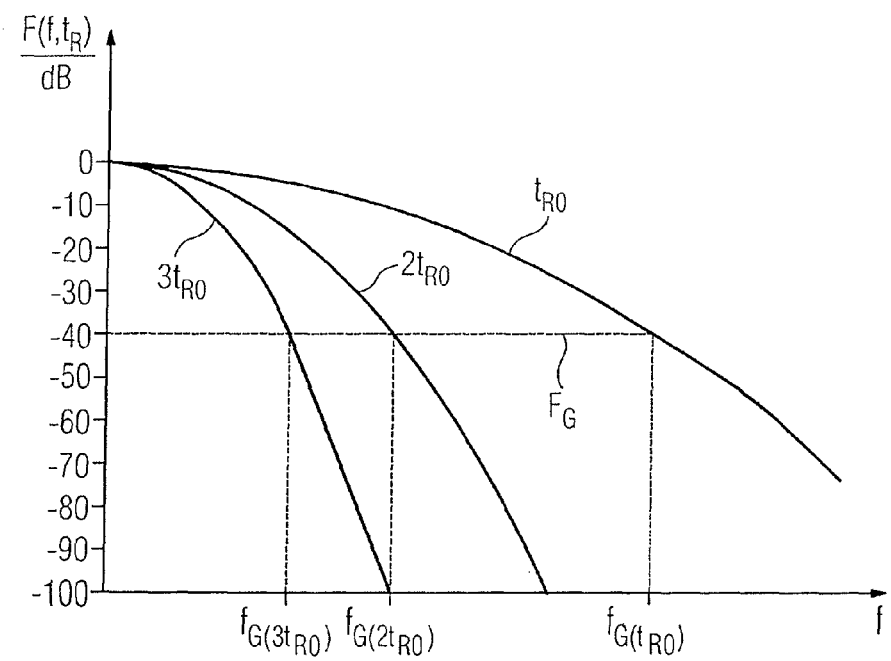
FIG. 2 is an exemplary graphical plot of the amplitude characteristics (frequency spectra) of three peaks with different retention times.

FIG. 2 shows that, according to Eq. 5, the amplitude characteristic F (f, $t_R$)/dB of a peak decreases with an increasing retention time $t_R$, so that with an increasing retention time $t_R$ a smaller bandwidth is required to perform signal processing in a microprocessor or other similar computing device. In order to establish the bandwidth for the signal processing, a limit frequency $f_G$ at which the amplitude characteristic F (f, $t_R$)/dB has decreased to a predetermined limit value $F_G$ is selected. If, for example, $F_G = -40$ dB is selected, then about 99% of the signal energy still lies above this limit value in the amplitude characteristic and the signal distortion to be expected is minimal. With $F_G = -40$ dB, Eq. 5 establishes the following relationship for the limit frequency:

$$f_{G(-40dB)}(t_R) = \frac{\sqrt{40/4.343}}{2\pi \cdot h \cdot K \cdot t_B}. \quad \text{Eq. 6}$$

Knowing the height h and the factor K of a single peak, a universal filter can be developed for all peaks P of the chromatogram, the limit frequency $f_G$ of which is varied as a function of the retention time $t_R$.

As will be explained below, the factor K is determined with the aid of a suitable individual peak by using the relationship of Eq. 2.

Figure 3:
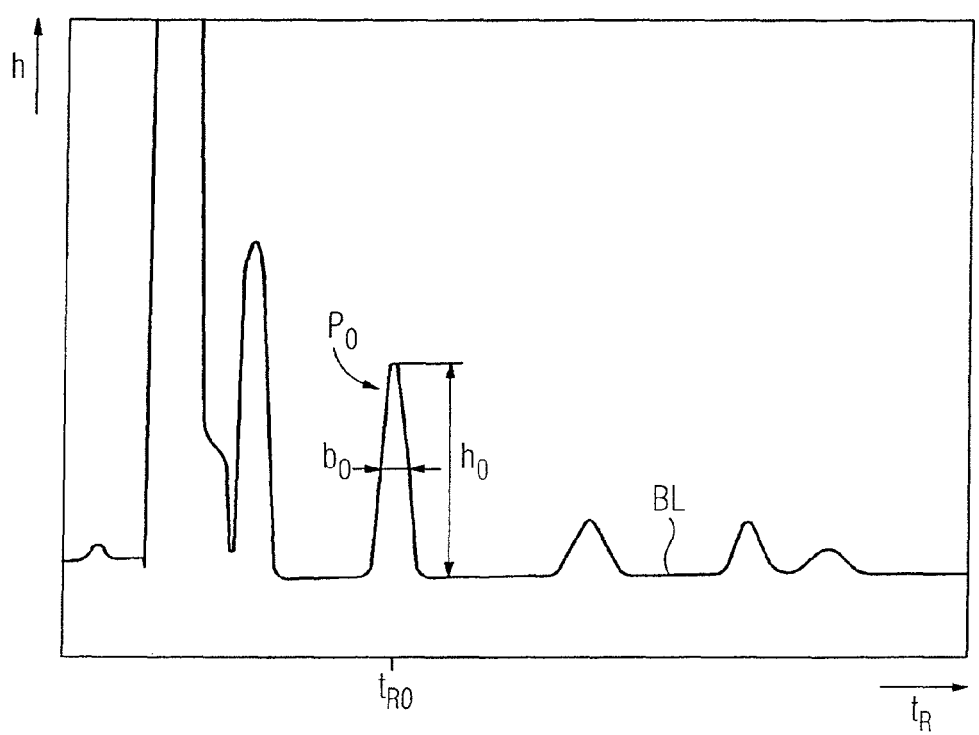
FIG. 3 is a graphical plot of a detail of a further chromatogram.
Figure 4:
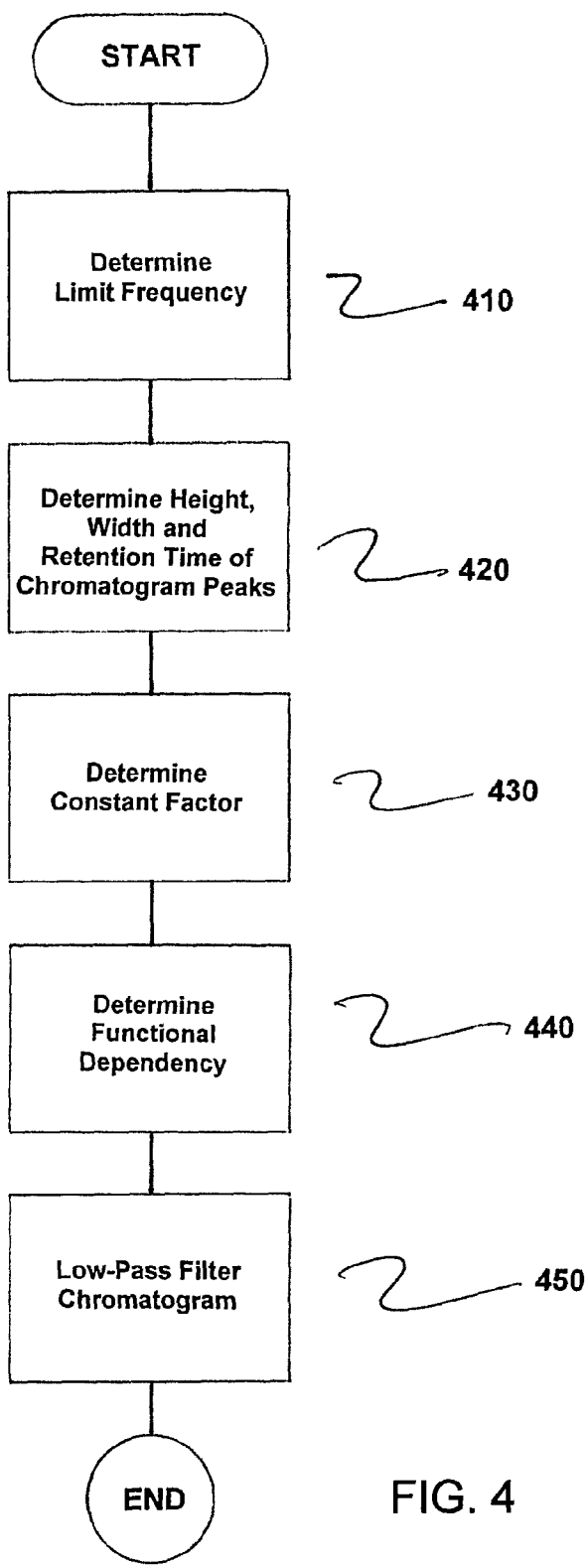
FIG. 4 is a flow chart of the method in accordance with the invention.

FIG. 3 shows an enlarged detail of another chromatogram, which was recorded into a device, such as a memory, under the same conditions as that according to FIG. 1. The peak height $h_0$, peak width $b_0$ at half peak height and the retention time $t_{R0}$ of a representative individual peak $P_0$ are measured, the following exemplary values being obtained:

$h_0 = 0.021$ $b_o = 0.8$ s $t_{R0} = 37.64$ s.

With $b = 2\sigma\sqrt{2\ln 2}$, this gives the following for the standard deviation $\sigma_o$ of the associated Gaussian function:

$\sigma_0 = 0.34$ s.

By using Eq. 4, the following is obtained for the factor K:

$$K = \frac{\sigma_0}{h_0 \cdot t_{R0}} = \frac{0.34s}{0.021 \cdot 37.64s} = 0.043.$$

The following is therefore obtained according to Eq. 6 for the limit frequency $f_{G\,(-40\,dB)}$, or the −40 dB bandwidth of the selected peak $P_0$:

$$\bar{z}_{G(-40dB)}(t_{F0}) = \frac{\sqrt{40/4.343}}{2\pi \cdot h_0 \cdot K \cdot t_{R0}}$$
$$= \frac{\sqrt{40/4.343}}{2\pi \cdot 0.021 \cdot 0.43 \cdot 37.64\varepsilon}$$
$$= 1.42 \text{ Hz}.$$

All signal components with frequencies greater than 1.42 Hz can therefore be removed by suitable signal processing from the peak $P_0$ considered here by filtering with virtually no loss of information, the signal/noise ratio or the detection limit being increased.

The entire chromatogram of FIG. 1 can now be lowpass-filtered with the limit frequency varied in accordance with Eq. 6 as a function of the retention time $t_R$.

$$f_{G(-40dB)}(t_R) = \frac{\sqrt{40/4.343}}{2\pi \cdot h_0 \cdot K \cdot t_R} = 53.489 \cdot \frac{1}{t_F}. \qquad \text{Eq. 7}$$

To this end, for example, an FIR filter may be used. With a moving average, the following applies for the −3 dB limit frequency $f_c$ of the FIR filter:

$$f_0 \approx \frac{f_A}{2N_F}, \qquad \text{Eq. 8}$$

where $f_A$ denotes the sampling frequency of the analog/digital conversion and $N_F$ denotes the number of sampled values of the chromatogram that are used for the averaging. By using Eq. 7 and Eq. 8, with $f_c = f_{G\,(-40\,dB)}(t_R)$, the following filter length to be varied with the retention time $t_R$ is obtained:

$$N_r = \frac{f_A}{2f_{G(-40dB)}(t_\lambda)} = 0.009348 \cdot f_A \cdot t_B,$$

where $N_F$ is rounded to an integer.

The signal/noise ratio, or the detection limit, is thereby increased by a factor of:

$$\frac{S}{N} = \sqrt{N_F}.$$

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A method for improving peak resolutions of a chromatogram produced by a detector arranged at an outlet of a process gas chromatographic separating apparatus, comprising:
   a) guiding a sample of a substance mixture to be analyzed through the process gas chromatographic separating apparatus;
   b) producing the chromatogram with a peak of the sample of the substance mixture detected by the detector arranged at the outlet of the process gas chromatographic separating apparatus;
   c) providing the process gas chromatographic separating apparatus with a Fourier transform of a Gaussian function, said Gaussian function having a standard deviation and approximately describing the shape of the peak in the chromatogram in the time-domain, and said Fourier transform describing a frequency spectrum of the peak and being provided as a function of frequency and the standard deviation;
   d) identifying, by a processor of the process gas chromatographic separating apparatus, a limit frequency at which the Fourier transform has decreased to a predetermined limit value, said limit frequency being a function of the predetermined limit value and the standard deviation;
   e) determining, by the processor of the process gas chromatographic separating apparatus, a height $h_0$, width and retention time $t_{R0}$ of one of (i) an individual peak of the chromatogram and (ii) a chromatogram previously recorded under identical conditions;
   f) determining, at the processor of the process gas chromatographic separating apparatus, a constant factor K based on a first predetermined relationship $\sigma_0/h_0 = K \cdot t_{R0}$, where $\sigma_0$ is the standard deviation of the Gaussian function that matches the individual peak;
   g) determining, at the processor of the process gas chromatographic separating apparatus, a functional dependency of the limit frequency on a retention time as a variable quantity in accordance with a second predetermined relationship, said second relationship being based on the identified limit frequency, the determined constant factor K and the first predetermined relationship in which the retention time tRo of the individual peak is substituted by said retention time as a variable quantity;
   h) low-pass filtering the chromatogram in the process gas chromatographic separating apparatus with the limit frequency as a function of the retention time as the variable quantity such that isolated individual peaks of the chromatogram having improved peak resolutions are generated at each operation of the process gas chromatographic separating apparatus; and
   i) determining a concentration of the sample of the substance mixture based on the isolated individual peaks of the chromatogram having the improved peak resolutions.

2. The method as claimed in claim 1, wherein the low-pass filtering is performed by a finite impulse response filter having a filter length varied in accordance with the limit frequency as a function of the second retention time.

* * * * *